United States Patent [19]
Good et al.

[11] Patent Number: 6,084,153
[45] Date of Patent: *Jul. 4, 2000

[54] PLANTS HAVING ENHANCED NITROGEN ASSIMILATION/METABOLISM

[75] Inventors: Allen G. Good, Edmonton; Virginia L. Stroeher, Calgary, both of Canada; Douglas G. Muench, Pullman, Wash.

[73] Assignee: The Governors of the University of Alberta, Edmonton, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/599,968

[22] Filed: Feb. 14, 1996

[51] Int. Cl.$^7$ .............................. A01H 1/00; C07H 21/04; C12N 15/00; C12N 15/82
[52] U.S. Cl. .......................... 800/290; 800/278; 800/289; 435/320.1; 435/468; 536/24.1
[58] Field of Search ...................................... 800/200, 205, 800/235, 250, 255, DIG. 9, DIG. 16, DIG. 17, DIG. 23, DIG. 24, DIG. 26, DIG. 40, 278, 289, 290; 435/320.1, 172.3, 172.1, 410, 412, 414, 415, 417, 419, 468; 935/6, 22, 67, 64; 536/23.1, 24.1

[56] References Cited

U.S. PATENT DOCUMENTS 5,256,558  10/1993  Coruzzi et al. ..................... 435/252.33

FOREIGN PATENT DOCUMENTS 1732188  of 1988  Australia .
9509911  4/1995  WIPO .

OTHER PUBLICATIONS

Watson et al. Benjamin/Cummings, Publishing Co., Menlo Park, CA, p. 313, 1987.

Lam et al, "Use of Arabidopsis Mutants and Genes to Study Amide Amino Acid Biosynthesis", The Plant Cell 7:887–898 Jul. 1995.

Muench and Good "Purification and characterization of Anerobically Induced Alanine Aminotransferase from Barley Roots" Plant Physiol 99:1520–1525, 1992.

Vauler berghe et al, "Anaerobic Metabolism in the N–limited Green Algae Selenstrum minutum", Plant Physiol 95:655–658 1991.

Crawford "Nitrate: Nutrient and Signal for Plant Growth" Plant Cell 7:859–868, Jul. 1995.

Cheng et al "A new locus (NIA1) in Arabidopois thaliana encoding nitrate reductase" The EMBO J. 7:3309–3314, 1988.

Zehnacker et al "Purification and properties of tobacco ferredoxin–dependent glutamate synthase and isolation of corresponding cDNA clones." Planta 187:266–274 (1992.

Peterman et al "The Glutamine Synthetase gene family of Arabidopsis Thaliana: Light Regulation and Differential Expression in Leaves, Roots and Seeds",—Mol Gen Genet (1991) 230: 145–154.

Muench et al "Hypoxically Inductible Barley Alanine Aminotransferase: cDNA Cloning and Expression Analysis"—Plant Molecular Biology 24:417–427 1994.

Eckes et al "Overproduction of Alfalfa Glutamine Synthetase in Transgenic Tobacco Plants"—Mol Gen Genet (1989) 217:263–268.

Hemon et al "Targeting of Glutamine Synthetase to the Mitochondria of Transgenic Tobacco"—Plant Molecular Biology 15: 895–904, 1990.

Hirel et al "Forcing Expression of a Soybean Roof Glutamine Synthetase Gene in Tobacco Leaves Induces a Native Gene Encoding Cytosolic Enzyme", Plant Molecular Biology 20: 207–218, 1992.

Temple et al "Nodulation of Glutamine Synthetase Gene Expression in Tobacco by the Introduction of an Alfalfa Glutamine Synthetase Gene in sense and Antisense Orientation: Molecular and Biochemical Analysis"—Mol Gen Genet (1993) 236:315–325.

Guerrero et al "Tissue Specific Expression of a Plant Turqor– Responsive Gene with Amino Acid Sequence Homology to Transport–Facilitating Proteins", Plant Molecular Biology 21: 929–935, 1993.

Cheng et al "Differential Expression of the Two Arabidopsis Nitrate Reductase Genes", Plant Physiol. (1991) 96, 275–279.

Stroeher et al "Molecular Cloning and Expression of a Turqor–Responsive Gene in Brassica Napus"—Plant Molecular Biology 27:541–551, 1995.

*Primary Examiner*—Bruce R. Campell
*Attorney, Agent, or Firm*—Lahive & Cockfield, LLP; Elizabeth A. Hanley, Esq.

[57] ABSTRACT

A genetic construct is taught which contains a nitrogen assimilation and/or metabolism gene and a promoter for the gene which is inducible under conditions where it would be beneficial to take-up, store or use nitrogen. The promoter can be, for example, induced by the presence of nitrate or other form of nitrogen and will be induced by application of a nitrogenous fertilizer. The stress inducible promoter btg-26 is also taught. Promoter btg-26 is isolated from the Brassica turgor gene—26 and exhibits osmotic-stress induced expression.

11 Claims, 8 Drawing Sheets

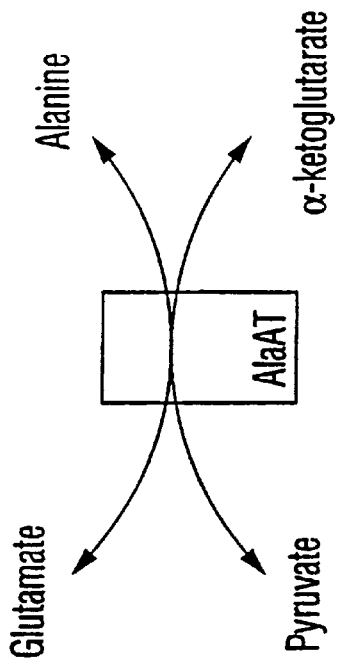

FIG. 2

```
GTCGACCTGCAGGTCAACGGATCCTAATCGGGTATATCCCGACCCGAAAAGAAACGTAGGACACGTG    -250
ACAAAACTTCATATGATCCGAGTGAATCAAGCCAAAAGGGGATTGACACAACAGCTCAGCTTTCGTTTT  -180
CGGTCCAATCGCTGTTCCAACTTTACTTACAAGTCGTACACGTCTCTCTCTCTCTCTCTCACTC       -110
ACTTCCTCTTATAAAGACTCTGATCAAACGTATAATCGGAAAACTCCATTCTTTGATACCATCGATAA   -40
TACTAAGAGAGGTGATTGATTCTTTAATCACTGTTTGATCCTTAACTTTGATCCATTACTCTGTTCA     31
                                  +1→
ATCATTTTTGTAGAG
```

FIG. 3

```
GGCCACAAAACCGCGGAAAGAGATAGACGGACAGCTAGAGGCGTCGGAAGATACTCGCTGCTCTGCCGCCCCTCGTCTCTTAGTTGATCTCGCC         94
ATGGCTGCCACCGTCGCCGTGGACAACCTGAACCCCAAGGTTTTAAAATGTGAGTATGCTGTGCGTGGAGAGATTGTCATCCATGCTCAGCGCTTG        190
 M  A  A  T  V  A  V  D  N  L  N  P  K  V  L  K  C  E  Y  A  V  R  G  E  I  V  I  H  A  Q  R  L         32
CAGGAACAGCTCAAAGACTCAACCAGGTCTCTACCTTTTGATGAGATCCTCTATTGTAACATTGGAACCCACAATCTCTTGGTCAGCAACCAGTT        286
 Q  E  Q  L  K  T  Q  P  G  S  L  P  F  D  E  I  L  Y  C  N  I  G  N  P  Q  S  L  G  Q  Q  P  V         64
ACATTCTTCAGGGAGGTTCTTGCCCTTTGTGATCATCCAGATCTGTTGCAAAGAGAGGAAATCAAAACATTGTTCAGTGCTGATTCTATTTCTGA        382
 T  F  F  R  E  V  L  A  L  C  D  H  P  D  L  L  Q  R  E  E  I  K  T  L  F  S  A  D  S  I  S  R         96
GCAAAGCAGATTCTGCCATGATACCTGGAAGACAACAGGAGCATACAGCCAGGTATTAAAGGACTTCGTGATGCAATTGCTTCTGGG              478
 A  K  Q  I  L  A  M  I  P  G  R  A  T  G  A  Y  S  H  S  Q  G  I  K  G  L  R  D  A  I  A  S  G        128
ATCGCTTCACGAGATGGATTCCCTGCTAATGCTGATGACATTTTCTCACAGATGGAGCAAGTCCTGCACCTGATGATGCAATTACTGATA            574
 I  A  S  R  D  G  F  P  A  N  A  D  D  I  F  L  T  D  G  A  S  P  G  V  H  L  M  M  Q  L  L  I        160
AGGAATGAGAAAGATGGCATTCTTGTCCCGATTCCTCAGTACCCCTTGTACTCGGCTTCTTCATGGCGGAGCTCTTGTCCCATACTAT             670
 R  N  E  K  D  G  I  L  V  P  I  P  Q  Y  P  L  Y  S  A  S  I  A  L  H  G  G  A  L  V  P  Y  Y        192
CTCAATGAATCGACGGCTGGGGTTTGGAACTTAAGAACAACTTGAAGAAGCATCGGTCAAGAGAGCATCAACGTTAGGGCTTTGGTG              766
 L  N  E  S  T  G  W  G  L  E  T  S  D  V  K  K  Q  L  E  D  A  R  S  R  G  I  N  V  R  A  L  V        224
GTTATCAATCCAGGAAATCCAACTGGACAGGTACTTGCTGAAGAAAACCAATATGACATAGTGAAGTTCTGCAAAAATGAGGGTCTTGTTCTTA        862
 V  I  N  P  G  N  P  T  G  Q  V  L  A  E  E  N  Q  Y  D  I  V  K  F  C  K  N  E  G  L  V  L  L        256
GCTGATGAGGTATACCAAGAGAACATCTATGTTGACAACAAGAAATTCCACTCTTTCAAGAAGATAGTGAGATCCTTGGGATACGGCGAGGAGGAT     958
 A  D  E  V  Y  Q  E  N  I  Y  V  D  N  K  K  F  H  S  F  K  K  I  V  R  S  L  G  Y  G  E  E  D        288
```

FIG. 5

```
CTCCCTCTAGTATCATATCAATCTGTTCTTAAGGATATATTATGGTGAGTGTGGTAAAGAGGTGGTTACTTGAGATTACTGGCTTCAGTGCTCCA    1054
 L  P  L  V  S  Y  Q  S  V  S  K  G  Y  Y  G  E  C  G  K  R  G  G  Y  F  E  I  T  G  F  S  A  P     320

GTAAGAGAGCAGATCTACAAATAGCATCAGTGAACCTATGCTCCAATATCACTGGCCAGATCCTTGTCATGAACCCACCAAAGGCT            1150
 V  R  E  Q  I  Y  K  I  A  S  V  N  L  C  S  N  I  T  G  Q  I  L  A  S  L  V  M  N  P  P  K  A    352

AGTGATGAATCATACGCTTCATACAAGGCAGAAAAAGATGGAATCCTCGCATCTTTAGCTCGTCGTGCGAAGGCATTGGAGCATGCATTCAATAAA   1246
 S  D  E  S  Y  A  S  Y  K  A  E  K  D  G  I  L  A  S  L  A  R  R  A  K  A  L  E  H  A  F  N  K    384

CTTGAGGGAATTACTTGCAACGAGGCTGAAGGAGCAATGTACGTGTTCCCTCAAATCTGTCTGCCACAGAAGGCAATTGAGGCTGTAAAGCTGCT    1342
 L  E  G  I  T  C  N  E  A  E  G  A  M  Y  V  F  P  Q  I  C  L  P  Q  K  A  I  E  A  A  K  A  A    416

AACAAAGCACCTGATGCATTCTATGCTCTTCGTCTCCGAGTCGACTGAATCAGGATTGGCCAGGTTCCTGGCACA                         1438
 N  K  A  P  D  A  F  Y  A  L  R  L  L  E  S  T  G  I  V  V  P  G  S  G  F  G  Q  V  P  G  T       448

TGGCACTTCAGGTGCACGATCCTTCCGCAGGAGGATAAGATCCCGGCAGTCATCTCCCGCTTCATCGAGGCGTTCATGTCAGAGTAT            1534
 W  H  F  R  C  T  I  L  P  Q  E  D  K  I  P  A  V  I  S  R  F  T  V  F  H  E  A  F  M  S  E  Y    480

CGTGACTAAACTGGTGCAACATGTGGATTACATACAACCCTCATGGGTTTTCGTAGGCGTTCTTGGTTTTGCCCCCCCCCCTTCTCTCTC         1630
 R  D                                                                                                482

TCTCTCTCTGACAGCATCCCTCCCTAGATGAGACAAAATAAAGCAAAGCCATGTCATCCTTAAAAAAAAAA      1701
```

PLANTS HAVING ENHANCED NITROGEN ASSIMILATION/METABOLISM

FIELD OF THE INVENTION

The present invention relates to genetic engineering of plants to display enhanced agronomic characteristics and, in particular, the genetic engineering of plants to display enhanced agronomic characteristics by enhancing the nitrogen assimilatory and metabolism capacities of the plants. The present invention also relates to an inducible promoter and, in particular, a promoter element which exhibits osmotic stress inducible expression.

BACKGROUND OF THE INVENTION

A. Nitrogen Assimilation and Metabolism

In many ecosystems, both natural and agricultural, the primary productivity of plants is limited by the three primary nutrients, nitrogen, phosphorous and potassium. The most important of these three limiting nutrients is usually nitrogen. Nitrogen sources are often the major components in fertilizers (Hageman and Lambert, 1988, I. Corn and Corn Improvement, 3rd ed., Sprague & Dudley, *American Society of Agronomy*, pp. 431–461). Since nitrogen is usually the rate-limiting element in plant growth, most field crops have a fundamental dependence on inorganic nitrogenous fertilizer. The nitrogen source in fertilizer is usually ammonium nitrate, potassium nitrate, or urea. A significant percentage of the costs associated with crop production results from necessary fertilizer applications. However, it is known that most of the nitrogen applied is rapidly depleted by soil microorganisms, leaching, and other factors, rather than being taken up by the plants.

Nitrogen is taken up by plants primarily as either nitrate ($NO_3^-$) or ammonium ($NH_4^+$). Some plants are able to utilize the atmospheric $N_2$ pool through a symbiotic association with $N_2$-fixing bacteria or ascomycetes. In well aerated, non-acidic soils, plants take up $NO_3^-$ which is converted to $NH_4^+$. In acidic soils, $NH_4^+$ is the predominate form of inorganic nitrogen present and can be taken up directly by plants. $NH_4^+$ is then converted to glutamine and glutamate by the enzymes glutamine synthetase (GS) and glutamate synthase (GOGAT). The glutamine and glutamate can be converted into a variety of amino acids, as shown in FIG. 1.

Although some nitrate and ammonia can be detected in the transporting vessels (xylem and phloem), the majority of nitrogen is first assimilated into organic form (e.g., amino acids) which are then transported within the plant. Glutamine, asparagine and aspartate appear to be important in determining a plants ability to take up nitrogen, since they represent the major long-distance nitrogen transport compounds in plants and are abundant in phloem sap. Aside from their common roles as nitrogen carriers, these amino acids have somewhat different roles in plant nitrogen metabolism. Glutamine is more metabolically active and can directly donate its amide nitrogen to a large number of substrates. Because of this reactivity, glutamine is generally not used by plants to store nitrogen. By contrast, asparagine is a more efficient compound for nitrogen transport and storage compared to glutamine because of its higher N:C ratio. Furthermore, asparagine is also more stable than glutamine and can accumulate to higher levels in vacuoles. Indeed, in plants that have high nitrogen assimilatory capacities, asparagine appears to play a dominant role in the transport and metabolism of nitrogen (Lam et al, 1995, *Plant Cell* 7: 887–898). Because of its relative stability, asparagine does not directly participate in nitrogen metabolism, but must be first hydrolysed by the enzyme asparaginase (ANS) to produce aspartate and ammonia which then can be utilized in the synthesis of amino acids and proteins.

However, in addition to aspartate and asparagine, a number of other amino acids can act as storage compounds. The total amount of free amino acids has been shown to change with specific stresses, both biotic and abiotic, different fertilizer regimes and other factors (Bohnert et al., 1995, *Plant Cell* 7:1099–1111). For example, during drought stress many plants maintain their turgor by osmotic adjustment (Turner, 1979, *Stress Physiology in Crop Plants*, pp. 181–194). Osmotic adjustment, i.e. a net increase in solutes leading to a lowering of osmotic potential, is one of the main mechanisms whereby crops can adapt to limited water availability (Turner, ibid; Morgan, 1984, *Annu Rev Plant Physiol* 35: 299–319). The solutes that accumulate during osmotic adjustment include sugars, organic acids and amino acids, such as alanine, aspartate and proline and glycine betaine (Good and Zaplachinski, 1994, *Physiol Plant* 90: 9–14; Hanson and Hitz, 1982, *Annu Rev Plant Physiol* 33: 163–203; Jones and Turner, 1978, *Plant Physiol* 61: 122–126). Corn, cotton, soybean and wheat have all demonstrated osmotic adjustment during drought (Morgan, ibid.). One of the best characterized osmoregulatory responses is the accumulation of proline (Hanson and Hitz, ibid.). In some tissues, proline levels increase as much as 100-fold in response to osmotic stress (Voetberg and Sharp, 1991, *Plant Physiol* 96: 1125–1130). The accumulation of proline results from an increased flux of glutamate to pyrroline-5-carboxylate and proline in the proline biosynthetic pathway, as well as decreased rates of proline catabolism (Rhodes et al., 1986, *Plant Physiol* 82:890–903; Stewart et al., 1977, *Plant Physiol.* 59:930–932). The concentrations of alanine and aspartate have been shown to increase 3.6 and 4.1-fold, respectively, during drought stress in *Brassica napus* leaves, whereas glutamate levels increased 5.5-fold (Good and Maclagan, 1993, *Can J Plant Sci* 73: 525–529). Alanine levels declined after rewatering of the plants whereas aspartate levels remained high. Pyruvate levels showed a similar pattern, increasing 2.2-fold after 4 days of drought, followed by the return to control levels upon rehydration. However, 2-oxoglutarate levels remained relatively constant during drought stress and rehydration. One of the factors that may determine the value of a specific amino acid as an osmoprotectant may be its use as a carbon or nitrogen storage compound.

Alanine is one of the common amino acids in plants. In Brassica leaves under normal conditions, alanine and aspartate concentrations are roughly equal and have been found to be twice that of asparagine concentrations. In comparison, glutamate levels were double that of alanine or aspartate (Good and Zaplachinski, ibid.). Alanine is synthesized by the enzyme alanine aminotransferase (AlaAT) from pyruvate and glutamate in a reversible reaction (Goodwin and Mercer, 1983, *Introduction to Plant Biochemistry 2nd Ed.*, Pergamon Press, New York, N.Y., pp. 341–343), as shown in FIG. 2. In addition to drought, alanine is an amino acid that is known to increase under other specific environmental conditions such as anaerobic stress (Muench and Good, 1994, *Plant Mol. Biol.* 24:417–427; Vanlerberge et al., 1993, *Plant Physiol.* 95:655–658). Alanine levels are known to increase substantially in root tissue under anaerobic stress. As an example, in barley roots alanine levels increase 20 fold after 24 hours of anaerobic stress. The alanine aminotransferase gene has also been shown to be induced by light in broom millet and when plants are recovering from nitrogen stress (Son et al., 1992, *Arch Biochem Biophys*

289:262–266). Vanlerberge et al. (1993) have shown that in nitrogen starved anaerobic algae, the addition of nitrogen in the form of ammonia resulted in 93% of an $N_{15}$ label being incorporated directly into alanine. Thus, alanine appears to be an important amino acid in stress response in plants.

The nitrate transporter genes, nitrate reductase (NR) and nitrite reductase (NiR) (Crawford, 1995, *Plant Cell* 7:859–868; Cheng et al, 1988, *EMBO J* 7:3309–3314) have been cloned and studied, as have many of the genes encoding enzymes involved in plant nitrogen assimilation and metabolism. Glutamine synthetase (GS) and glutamate synthetase (GOGAT) have been cloned (Lam et al., ibid.; Zehnacker et al., 1992, *Planta* 187:266–274; Peterman and Goodman, 1991, *Mol. Gen. Genet.* 230:145–154) as have asparaginase (ANS) and aspartate aminotransferase (AspAT) (Lam et al., ibid; Udvardi and Kahn, 1991, *Mol. Gen. Genet.* 231:97–105). An asparagine synthetase (AS) gene has been cloned from pea (Tsai and Coruzzi, 1990, *EMBO J* 9:323–332). Glutamate dehydrogenase has been cloned from maize (Sakakibara et al., 1995, *Plant Cell Physiol.* 36(5):789–797. Alanine aminotransferase has been cloned by Son et al. (1993, *Plant Mol. Biol.* 20:705–713) and by Muench and Good, (1994 *Plant Mol. Biol.* 24:417–427). Among the plant nitrogen assimilation and utilization genes, the most extensively studied are the glutamine synthetase and asparagine synthetase genes.

In plants, genetic engineering of nitrogen assimilation processes has yielded varied results. Numerous studies examining constitutive overexpression of glutamine synthetase (GS) have failed to report any positive effect of its overexpression on plant growth. These studies include, for example: Eckes et al. (1989, *Molec. Gen. Genet.* 217:263–268) using transgenic tobacco plants overexpressing alfalfa GS; Hemon et al. (1990, *Plant Mol. Biol.* 15:895–904) using transgenic tobacco plants overexpressing bean GS in the cytoplasm or mitochondria; and Hirel et al. (1992, *Plant Mol. Biol.* 20:207–218) using transgenic tobacco plants overexpressing soybean GS. One study, by Temple et al (1993, *Mol. Gen. Genet.* 236:315–325), has reported increases in total soluble protein content in transgenic tobacco plants overexpressing an alfalfa GS gene and similar increases in total soluble protein content in transgenic tobacco plants expressing antisense RNA to a GS gene.

There has been a report that plants engineered to constitutively overexpress an alfalfa GS gene grow more rapidly than control, wild-type plants (Eckes et al., 1988, Australian published patent application no. 17321/88). Another report (Coruzzi and Brears 1994, WO 95/09911) introduced GS, GOGAT and AS constructs under the control of a constitutive Cauliflower Mosaic Virus 35S (CaMV35S) promoter. This document showed that the transgenic plants had increased fresh weight and growth advantage over controls. Thus, there appears to be no clear direction on the effect of constitutive overexpression of nitrogen assimilation enzymes on plant growth.

B. Turgor Responsive Promoters

Maintenance of normal growth and function in plants is dependent on a relatively high intracellular water content. Drought, low temperature and high salinity are all environmental stresses that alter cellular water balance and significantly limit plant growth and crop yield (Morgan, ibid.). Many physiological processes change in response to conditions that reduce cellular water potential, including photosynthesis, stomatal opening and leaf, stem and root growth (Hanson and Hitz, ibid.) Along with physiological responses, metabolic changes can also occur during water loss. One of the most notable changes is in the synthesis and accumulation of low molecular weight, osmotically active compounds, as noted above.

Changes in gene expression also occur during osmotic stress. A number of genes have recently been described that are induced by drought (reviewed by Skiver and Mundy, 1990, *Plant Cell* 2:503–512).

SUMMARY OF THE INVENTION

In one aspect, this invention involves a gene which comprises a nitrogen assimilation/metabolism pathway enzyme coding sequence operably associated with a promoter inducible under conditions where it is desirable that plants take up nitrogen. Such a genetic construct acts to confer to a plant or plant cell, into which it is introduced, enhanced nitrogen assimilation/metabolism properties which are inducible at times when it would be useful to enhance the plant's ability to take up, store and/or use nitrogen.

Such genetic constructs can be inserted into plant transformation vectors and/or introduced to plant cells. Transformed plants can be produced which contain the genetic construct of the present invention.

In accordance with a broad aspect of the present invention, there is provided a plant gene adapted for transcription and translation in a plant system comprising a nitrogen assimilation/metabolism enzyme coding sequence operably associated with a promoter inducible under conditions where it is desirable that plants assimilate/metabolize nitrogen.

In accordance with another broad aspect of the present invention, there is provided a method for producing a plant have inducible nitrogen assimilation and/or metabolism capabilities comprising: transforming a plant cell by introducing a genetic construct having a nitrogen assimilation/metabolism enzyme coding sequence operably associated with a promoter inducible under conditions where it is desirable that plants assimilate/metabolize nitrogen.

The promoter is selected to be inducible under any condition where it would be desirable to cause the plant to have enhanced nitrogen uptake, assimilation or use capabilities. For example, suitable promoters may include, but are not limited to, those which are induced by application of sources of nitrogen, stress inducible, wound inducible or induced by application of other chemicals. Transgenic plants containing the genetic construct of the present invention exhibit enhanced agronomic characteristics over control plants or plants having constitutively over-expressed nitrogen assimilation/metabolism genes. The particular agronomic characteristic which is enhanced usually depends on the nature of the promoter and can include enhanced stress tolerance and/or more efficient nitrogen uptake, storage or metabolism allowing the plants of the present invention to be cultivated with lower nitrogen fertilizer input and in nitrogen starved conditions or allowing faster growth, greater vegetative and/or reproductive yield under normal growing conditions.

In another aspect, the invention is directed to a promoter which is inducible under osmotic stress conditions. The promoter is isolated from *Brassica napus* and is known as the Brassica turgor gene 26 (btg-26) promoter. Thus, in accordance with another broad aspect of the present invention, there is provided a substantially pure or isolated Brassica turgor gene-26 promoter element which confers osmotic stress inducible expression of an operably associated enzyme, as well as functional portions thereof. The invention also provides for promoters homologous to the btg-26 promoter, genetic constructs containing the btg-26 promoter, and transgenic plant cells and plants which comprise the promoter of the invention. Thus, in accordance with another broad aspect of the present invention, there is provided a genetic construct containing a btg-26 promoter element operably associated with at least one coding sequence, wherein the coding sequence is not naturally associated with the element.

The promoter is inducible under conditions of osmotic stress and directs high levels of transcription in plant cells. The stress inducible expression of gene products offers many potential applications for the promoter sequence including, but not limited to, enhancement of stress tolerance in plants.

BRIEF DESCRIPTION OF THE DRAWINGS

FIG. 2: Pathway for alanine biosynthesis by the enzyme alanine aminotransferase (AlaAT) (From Goodwin and Mercer, 1983).

FIG. 3: DNA sequence of the *Brassica napus* btg-26 promoter.

FIG. 5: Nucleotide and deduced amino acid sequence of the AlaAT cDNA from barley.

DETAILED DESCRIPTION OF THE INVENTION

Figure 1:
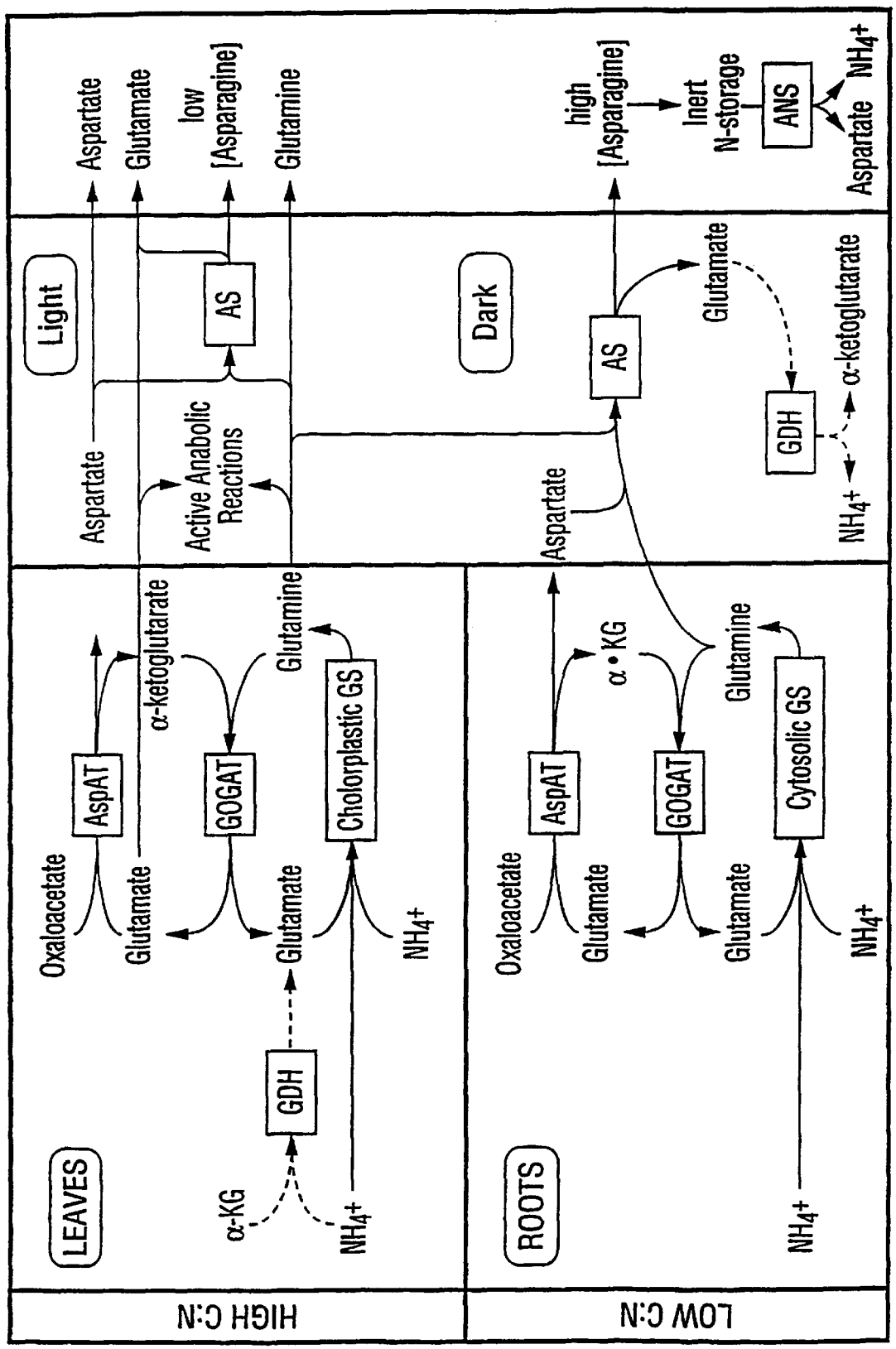
FIG. 1: Major pathways of nitrogen assimilation and metabolism in plants. (Adapted from Lam et al., 1995, *Plant Cell* 7: 889 where Arabidopsis is used as a model system). Some of the enzymes of the nitrogen assimilation and amide amino acid metabolism pathways are shown. Different isoenzymes are known for some of these enzymes which may play different roles under different environmental and tissue conditions. Nitrogen assimilation occurs primarily through the activities of glutamine synthetase (GS) and glutamate synthase (GOGAT). While not indicated as such, aspartate aminotransferase also catalyses the reverse reaction. The roles of glutamate dehydrogenase (GDH) are postulated, as indicated by the dashed lines.

In one aspect, the present invention is directed to a genetic construct having a coding sequence of a nitrogen assimilation/metabolism enzyme and a promoter sequence inducible under conditions where it is desirable for plants to take-up, store and/or use nitrogen. Such a gene can be introduced to a cloning or expression vector and used to transform plant cells or plants.

The promoter sequences useful in the present invention are those which regulate gene expression in response to a condition in which it would be desirable to cause a plant to assimilate and/or metabolize nitrogen and, for example, include, but are not limited to, promoters induced by specific environmental conditions, such as drought stress, osmotic stress, wound stress, heat stress, anaerobic stress, and salt stress; promoters induced upon the addition of nitrogen; or promoters induced by addition of other chemicals, such as for example auxin.

When used to transform plants, such genetic constructs can provide transformed plants which can assimilate and/or use nitrogen when it is most needed or beneficial. For example, where the promoter is a stress inducible promoter such as, for example, the drought-induced promoters 26 g from *Pisum sativum* (Guerrero and Mullet, 1988, *Plant Physiol,* 88:401–408; Guerrero et al., 1990, *Plant Mol Biol* 15: 11–26), trg-31 from tobacco (Guerrero and Crossland, 1993, *Plant Mol Biol* 21:929–935) or btg-26 from *Brassica napus* as discussed in Example 1 and shown in FIG. 3 and SEQ ID NO:1, the plant is induced to assimilate and/or metabolize nitrogen upon application of the stress. Such a plant thereby can have increased stress tolerance, such as by enhanced osmoregulation.

As another example, where the promoter is induced by the presence of nitrate, such as, for example, the nitrate reductase promoter (Cheng et al, 1988, ibid.; Cheng et al, 1991, *Plant Phsyiol.* 96:275–279), the plant will be induced to assimilate and/or use nitrogen upon application of a nitrogenous fertilizer. Alternately, or in addition, the promoter can be inducible, for example, by an exogenously applied chemical such as ABA (Marcotte et al, 1989, *Plant Cell* 1:969–976). This chemical could be included in nitrogenous fertilizer. Thus, plants can more efficiently utilize fertilizer input by rapidly taking up the nitrogen in the fertilizer and storing it at the time of application, to thereby reduce the amounts of nitrogenous fertilizer which are lost to leaching, etc. This may permit a reduction in the amount of nitrogenous fertilizer required to be applied to a crop, to obtain crop yields comparable to those obtained using normal cultivation techniques and plants which have not been modified according to the present invention. Additional agronomic advantages can include faster growth and crop yield, where nitrogenous fertilizer input is maintained at levels used in common crop cultivation techniques.

The inducible promoters useful in the present invention can be homologous or heterologous to the plant to which it is to be introduced. Multiple copies of the promoters can be used. The promoters may be modified, if desired, to alter their expression characteristics, for example, their expression levels and/or tissue specificity. In a preferred embodiment, the inducible promoter is ligated to another sequence, or otherwise modified or selected, to be repressed in the presence of light to create an inducible promoter which is active only in roots. The selected wild-type or modified inducible promoter may be used as described herein.

The genes of interest are those encoding enzymes in the assimilation and/or metabolism of nitrogen and, in particular, those which assimilate ammonia into amino acids or use the formed amino acids in biosynthetic reactions. These enzymes include, but are not limited to, glutamine synthetase (GS), asparagine synthetase (AS), glutamate synthase (also known as glutamate 2:oxogluturate amino transferase and GOGAT), asparaginase (ANS), glutamate dehydrogenase (GDH), aspartate aminotransferase (AspAT) (activities are shown in FIG. 1) and alanine aminotransferase (AlaAT) (activity shown in FIG. 2).

The nitrogen assimilation/metabolism genes can be used in their wild-type forms or can be altered or modified in any suitable way to achieve a desired plant improvement. These genes can be obtained from any source and can be homologous or heterologous to the plant cell into which it is to be introduced. Preferably, the gene is heterologous to the promoter to which it is linked, in that it is not linked to an unmodified, inducible promoter that the gene is naturally linked to.

In a plant of the present invention, the coding sequence can be a native copy of the desired enzyme which has had its regulatory region modified to be inducibly promoted or can be a native inducible promoter having been modified to be operably associated with a nitrogen assimilation/metabolism enzyme gene.

The genes can be modified in any suitable way to engineer a gene or plant with desirable properties. The gene is adapted to be transcribable and translatable in a plant system, for example, the gene contains all of the necessary polyadenylation sequences, start sites and termination sites which allow the coding sequence to be transcribed to mRNA (messenger ribonucleic acid) and the mRNA to be translated in the plant system. The gene constructs can be produced using methods known to those skilled in the art. The gene construct can advantageously contain one or more bacterial or plant-expressible selectable or screenable markers, such as a Kanamycin resistance gene, β-glucuronidase (GUS) genes and many others.

The gene can be inserted to a cloning or expression vector, and can be modified for such insertion. Examples of cloning or expression vectors are plasmids, cosmids, viral DNA or RNA, and minichromosomes.

The gene construct of the present invention can be introduced to a plant cell by any useful method. A large number of processes are available and are well known to deliver genes to plant cells. One of the best known processes involves the use of Agrobacterium or similar soil bacteria as a vector. Target tissues are co-cultivated with Agrobacterium which inserts the gene of interest to the plant genome. Such methods are well known in the art as illustrated by U.S. Pat. No. 4,940,838 by Schilperoort et al., Horsch et al. 1985, *Science* 227:1229–1231. Alternative gene transfer and transformation methods useful in the present invention include, but are not limited to liposomes, electroporation or chemical-mediated uptake of free DNA, targeted microprojectiles and microinjection. These methods are well documented in the prior art.

Cells that have been transformed with the gene construct of the present invention can be regenerated into differentiated plants using standard nutrient media supplemented with shoot-inducing or root-inducing hormone, using methods known to those skilled in the art.

Suitable plants for the practice of the present invention include, but are not limited to, canola, corn, rice, tobacco, soybean, cotton, alfalfa, tomato, wheat and potato. Of course, it would be understood a large number of plants could be advantageously engineered with the gene of the present invention. Transformed plants according to the present invention can be used for breeding, or for crop production.

While the genetic construct of the present invention can include any promoter which is inducible under conditions where it would be beneficial to express a nitrogen assimilation/metabolism gene, a novel promoter has been isolated which can be used in the genetic construct described hereinbefore or in other genetic constructs. The novel promoter is termed btg-26 and was found to be inducible by osmotic stresses such as heat shock, drought, salinity and ABA concentration. The present invention provides for: the btg-26 promoter element as depicted in FIG. 3 and SEQ ID NO:1, portions thereof or nucleic acid sequences homologous thereto; genetic constructs containing this promoter element; and transgenic plant cells and plants engineered to comprise the promoter of the invention.

Nucleotide sequences homologous to the btg-26 promoter described herein are those nucleic acid sequences which are capable of hybridizing to the nucleic acid sequence depicted in FIG. 3 (SEQ ID NO:1) in standard hybridization assays or are homologous by sequence analysis (at least 45% of the nucleotides are identical to the sequence presented herein). Homologous nucleotide sequences refer to nucleotide sequences including, but not limited to, promoter elements from other plant species or genetically engineered derivatives of the promoter element according to the present invention. The promoter element may be engineered to alter its activity, for example its level of expression. Such engineered promoters may be used, according to the invention.

The promoter of the present invention can be used to direct the expression of any gene product, as desired. Gene constructs containing the promoter element may contain other nucleic acid sequences, in addition to the coding sequence to which it is operably associated, such as for example 5' non-translated sequences and sequences encoding initiation sites or target peptides. The construct can also contain sequences necessary for transformation using Agrobacterium methods, as well as marker genes for bacterial or plant systems, as desired.

A gene construct containing the promoter can be introduced to a plant or plant cell by any useful transformation method, as noted hereinbefore, for introducing genetic material to plants. Transformed cells can be regenerated to differentiated plants using any useful method, as noted hereinbefore.

The following examples further demonstrate several preferred embodiments of this invention. While the examples illustrate the invention, they are not intended to limit the invention.

EXAMPLES

Example 1

Isolation and Characterization of Osmotic Stress-Induced Promoter

A *Brassica napus* (cv. Bridger) genomic DNA library (Clontech, Palo Alto, Calif.) was screened using standard techniques (Ausubel et al., 1989, Current Protocols in Molecular Biology, Wiley, Wiley, N.Y.) with the *Pisum sativum* 26g cDNA (complementary deoxyribonucleic acid) clone (Guerrero et al., ibid), $^{32}$P-labelled with a Random Primer Kit (Boehringer Mannheim, Laval, Quebec). A 4.4 kb SalI fragment containing the entire btg-26 gene was subcloned into the commercially available pT7T3-19U vector (Pharmacia Canada, Inc., Baie d'Urfe, Quebec, Canada) for further analyses.

Identification of a osmotic stress-induced promoter in *Brassica napus*

Several genes activated during drought stress have been isolated and characterized from different plant species. Most of these represent later-responding, ABA-inducible genes (reviewed by Skiver and Mundy, ibid.). Recently, however, an ABA-independent, cycloheximide-independent transcript, 26 g, was reported in *Pisum sativum* (Guerrero and Mullet, ibid; Guerrero et al., ibid). Because this gene does not require protein synthesis for activation, it is postulated that it represents an early factor in the drought signal transduction pathway. To isolate an osmotic stress induced promoter from *Brassica napus*, the cDNA clone representing the *P. sativum* 26 g gene (Guerrero et al., ibid) was used. Total RNA was isolated from the third leaf of whole plants that had been either watered continuously or dehydrated for four days. Using low stringency hybridization, RNA blot analysis identified a single 1.75 kb transcript that is greatly induced in droughted plants (data not shown). To determine if this mRNA represents a single copy gene in *B. napus*, genomic DNA was digested with EcoRI, HindIII or BglII and analyzed by DNA blot hybridization using the *P. sativum* 26 g cDNA. A single band was identified in each lane (data not shown). It was concluded that this transcript represents a single copy, drought-induced gene in *B. napus*. This gene is referred to as btg-26 (Brassica turgor gene—26).

Structure of btg-26 gene

To isolate the btg-26 gene, a *B. napus* genomic DNA library in EMBL-3 (Clontech, Palo Alto, Calif.) was screened with the *P. sativum* 26 g cDNA. From 40,000 plaques analyzed, a single positive clone was identified with an insert size of approximately 16 kb. A 4.4 kb SalI fragment containing the entire gene was subcloned. The promoter sequence of the btg-26 gene was determined by identification of the mRNA start site using primer extension (Ausubel, ibid.) and is shown in FIG. 3 and SEQ ID NO:1. In FIG. 3, the transcription start site is bolded, underlined and indicated by +1. The TATA box and CAAT box are in bold and double underlined. Postulated functional regions are underlined. The sequence of the btg-26 promoter, coding region and 3' region has been presented in Stroeher et al, (1995, *Plant Mol. Biol.* 27:541–551).

Expression analysis of btg-26

Figure 4A:
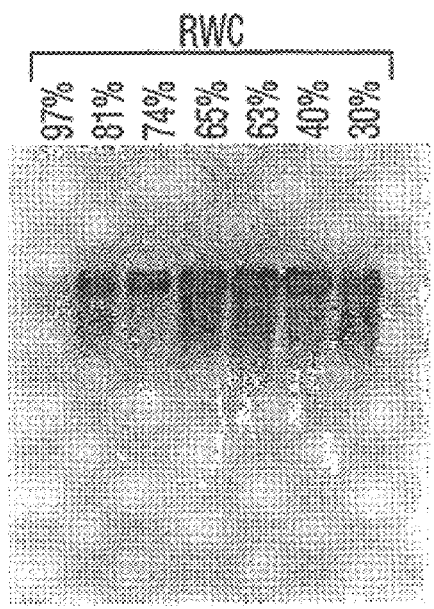
FIG. 4A: Northern blot analysis of btg-26 expression during droughting. Total RNA (10 mg) from leaf tissue taken from control plants having 97% relative water content (97% RWC) and plants dehydrated to the % RWC's as, indicated, was fractionated on a 1.2% agarose formaldehyde gel and probed with btg-26 genomic DNA.
Figure 4B:
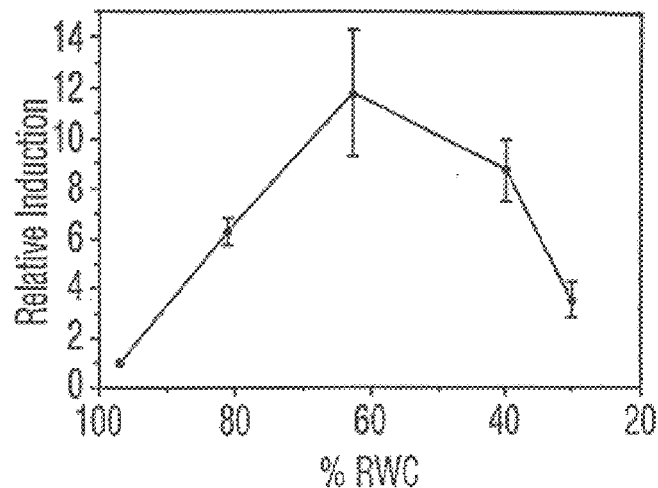
FIG. 4B: Quantitative analysis of btg-26 induction. Each time point represents the mean induction determined from three independent slot blots and two Northern blots. All blots were reprobed with a cyclophilin cDNA control to correct for loading error. Induction is determined relative to the level of expression in fully hydrated plants (97%).

Induction of btg-26 expression during droughting was examined by RNA blot analysis. Potted *B. napus* plants were naturally dehydrated by withholding water for various lengths of time. Whole leaves were used either to determine relative water content (RWC) of individual plants or to isolate total RNA. As shown in FIGS. 4A and 4B, btg-26 expression is induced rapidly during water loss, reaching a six-fold increase over expression in fully hydrated plants at 81% RWC, increasing to eleven-fold induction at 63% RWC. Further decreases in RWC were associated with a decrease in total amount of btg-26 transcript. At 30% RWC expression was only 3.5-fold over fully hydrated levels.

Figure 4C:
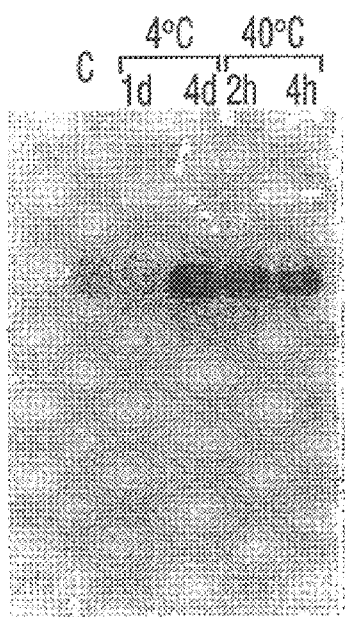
FIG. 4C: Northern blot analysis of btg-26 expression during cold acclimation and heat shock. Total RNA (10 mg) from leaf tissue taken from control plants (C) or plants exposed to 4° C. for one or four days or exposed to 40° C. for two or four hours. The RNA was fractionated on a 1.2% agarose formaldehyde gel and probed with btg-26 genomic DNA.
Figure 4D:
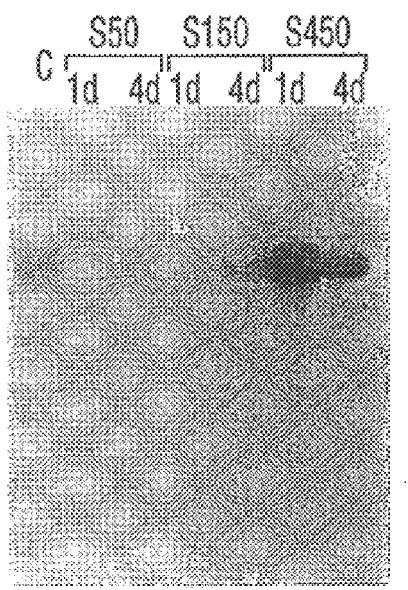
FIG. 4D: Northern blot analysis of btg-26 expression during salinity stress. Total RNA (10 mg) from leaf tissue taken from control plants (C) or plants exposed to salinity stress by watering with 50 mM NaCl (S50), 150 mM NaCl (S150) or 450 mM NaCl (S450) for one or four days. The RNA was fractionated on a 1.2% agarose formaldehyde gel and probed with btg-26 genomic DNA.

Because other physiological stresses alter intracellular water content, btg-26 expression was examined in *B. napus* plants exposed to cold, heat shock and salt stress. RNA blot analysis indicated that there was no change in btg-26 expression when plants were transferred from normal growth conditions to 4° C. for one day. However, plants left at 4° C. for four days showed a five-fold induction in btg-26 mRNA. A similar increase was seen when plants were shifted to 40° C. for two or four hours. These results are shown in FIG. 4C and demonstrate that expression of btg-26 is induced during temperature stress. To examine the effect of salt stress, plants were watered to capacity one day or four days with 50 mM, 150 mM, or 450 mM NaCl. The level of btg-26 expression was not affected by 50 mM NaCl regardless of length of exposure. However, growth in 150 mM NaCl caused a two-fold increase in btg-26 mRNA after four days. Exposure to 450 mM NaCl caused the most notable induction, twelve-fold after one day, dropping to four-fold after four days. Refer to FIG. 4D for Northern blots showing these results.

Figure 4E:
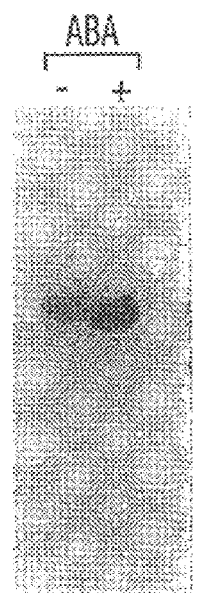
FIG. 4E: Northern blot analysis of btg-26 expression during exposure to abscisic acid (ABA). Total RNA (10 mg) from leaf tissue taken from plants soaked for one day in a solution containing either 0 µM (−) or 100 µM ABA (+). The RNA was fractionated on a 1.2% agarose formaldehyde gel and probed with btg-26 genomic DNA.

Finally, many drought-inducible genes are also ABA responsive. To examine the role of ABA in btg-26 expression, total RNA was isolated from individual leaves treated with or without ABA. In these experiments, leaves were cut at the petiole and placed in a solution of 0 µM, 50 µM or 100 µM ABA (mixed isomers, Sigma), 0.02% Tween-20 and pH 5.5 for 24 hours. As shown in FIG. 4E, btg-26 expression is induced 2.5-fold when exposed to 100 µM ABA. However, when leaves were exposed to 50 µM ABA, no induction of expression was observed (data not shown). These results indicate that btg-26 is ABA responsive, but that this responsiveness is concentration dependent.

Example 2

Creation of Drought-Induced Nitrogen Assimilation Constructs

This step involved the production of either constitutive or drought induced AlaAT constructs and the introduction of them into *Brassica napus* using Agrobacterium mediated genetic transformation. The approach of introducing specific sense or antisense cDNA constructs into plants to modify specific metabolic pathways has been used in a number of species and to modify a number of different pathways. (See Stitt & Sonnewald 1995 for a review; *Ann. Rev. of Plant Physiol. and Plant Mol. Biol.* 46:341–368). The AlaAT cDNA was introduced under the control of three different promoters. (1) The CaMV promoter which has been shown to be a strong constitutive promoter in a number of different plant species; (2) the btg-26 promoter described in Example 1 and (3) the trg-3 1 promoter which was isolated from tobacco by Guerrero and Crossland (ibid.). The CaMV promoter should result in the constitutive overexpression of AlaAT whereas btg-26 and trg-31 should induce over expression of AlaAT only under conditions of specific stresses, including drought stress.

Plasmid Constructs

The barley AlaAT cDNA clone 3A (As shown in FIG. 5 and Muench and Good, ibid) was cloned into the pT7T3-

Figure 6:
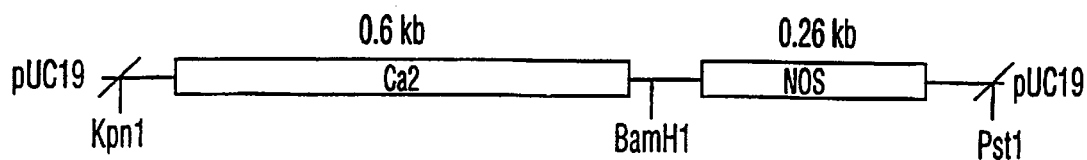
FIG. 6: Plasmid construct p25.

19U vector (Pharmacia Canada) and used for site directed metagenesis using two specific primers. Primer 1 introduced a BamH1 restriction site between nucleotides 48–53, while primer 2 was used to introduce a second BamH1 restriction site between nucleotides 1558–1563 (See FIG. 5). The 1510 bp fragment was then cloned into the vector p25 (FIG. 6) which had been cut with BamH1. p25 was a gift of Dr. Maurice Moloney (Univ. of Calgary, Calgary, Alta., Canada). This construct contains the double CaMV35S promoter, which has been shown to give high constitutive levels of expression, and NOS terminator inserted into the Kpn1 and Pst1 site of pUC19 with a BamH1, Xba1 and Pvu1 polylinker between the CaMV and NOS region of the plasmid. The resulting plasmid was called pCa2/AlaAT/NOS, as shown in FIG. 7A.

The plasmids ptrg-31/AlaAT/NOS and pbtg-26/AlaAT/NOS were created as follows. The trg-31 promoter was subcloned as a 3.0 kb Xba1/BamH1 fragment into the Xba1/BamH1 site of pCa2/AlaAT/NOS which had been digested with Xba1/BamH1 to release only the CaMV promoter, resulting in a 3 kb promoter fragment inserted in front of the AlaAT coding region. btg-26/AlaAT/NOS was created by inserting a BamH1 site at nucleotides +9 to +14 (see FIG. 3) and subcloning the 330 bp Kpn1/BamH1 fragment (from −320 to +10 in FIG. 3) into the Kpn1/BamH1 site of pCa2/AlaAT/NOS which had been digested to release the CaMV promoter. Plasmid constructs pbtg-26/AlaAT/NOS and ptrg-31/AlaAT/NOS and can be seen in FIGS. 7B and 7C, respectively.

Transformation and analysis of *Brassica napus* plants with AlaAT constructs.

Figure 7A:
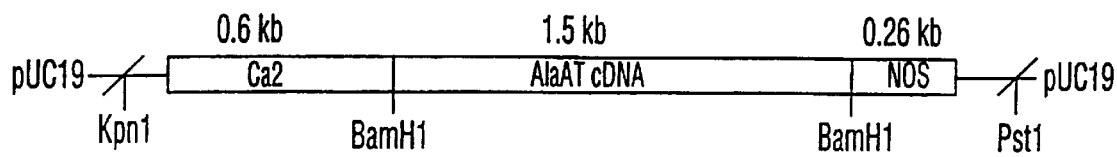
FIGS. 7A to 7C: Plasmid constructs containing the AlaAT coding region and the CaMV, btg-26 and trg-31 promoters that were used for the transformation of *Brassica napus* plants.
Figure 7B:
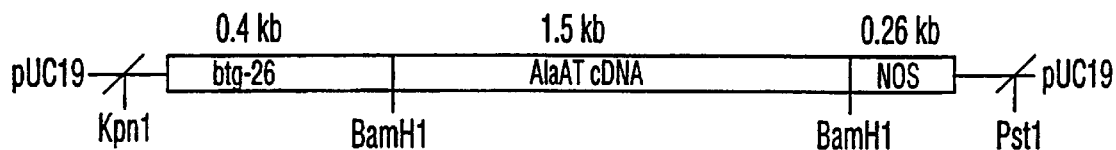
Figure 7C:
Figure 8:
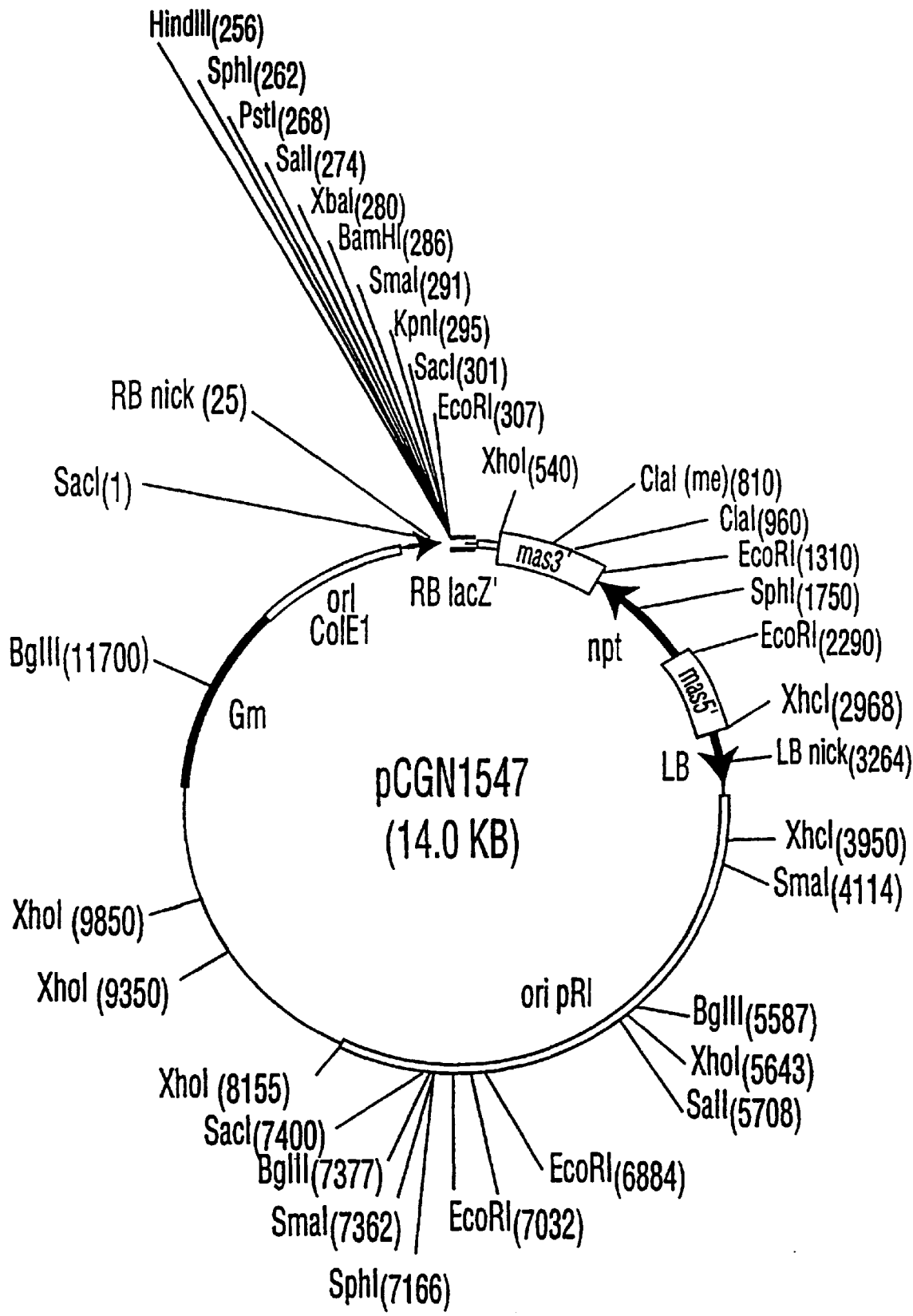
FIG. 8: Plasmid construct pCGN1547 used in producing the overexpressed/AlaAT or drought inducible/AlaAT transformants.

Once the three plasmids, as shown in FIGS. 7A, 7B and 7C, containing the AlaAT gene had been confirmed by restriction analysis and sequencing they were subcloned into the transformation vector pCGN1547 (FIG. 8). pCGN1547 is an Agrobacterium binary vector developed by McBride and Summerfelt (1990, *Plant Mol. Biol.* 14:269–276). pCGN1547 contains the neomycin phosphotransferase II (NPTII) gene which encodes Kanamycin resistance. These constructs were then introduced into the Agrobacterium strain EHA101 by electroporation using the protocol of Moloney et al. (1989, *Plant Cell Reports* 8:238–242). Confirmation that the Agrobacterium had been transformed with the pCGN1547 vector containing the specific construct was confirmed by polymerase chain reaction (PCR).

Transgenic plants were produced using a cotyledon transformation approach as described by Moloney et al. (ibid.). Kanamycin resistant plantlets were transferred to soil and then grown. The initial generation, or primary transformants, were referred to as the T0 generation and were allowed to self. Each subsequent generation was bagged to ensure selfing and referred to as the T1, T2 generation respectively. All putative T0 transgenic plants were tested for the insertion of the *Agrobacterium* construct using PCR primers that amplify the NPTII gene and by testing for NPTII activity as described by Moloney et al (ibid.).

Analysis of Transformed Brassica plants containing the AlaAT constructs:

Transgenic plants were assayed for AlaAT activity as follows. Extractions were carried out on ice as described previously (Good and Crosby, 1989, *Plant Physiol* 90:1305–1309). Leaf tissue was weighed and ground with sand in a mortar and pestle in extraction buffer containing 0.1M Tris-HCl (pH 8.5), 10 mM dithiothreitol, 15% glycerol and 10% (w/v) PVPP. The extract was clarified by centrifugation at 6,000 rpm and the supernatant was assayed for enzyme activity. AlaAT assays were performed in the alanine to pyruvate direction as described previously (Good and Crosby, ibid) using alanine to start the reaction.

After transformation 20 Ca2/AlaAT/NOS, 24 btg-26/AlaAT/NOS and 21 trg-31/AlaAT/NOS plants were produced which appeared to be transformed, based on the amplification of an NPTII PCR product and NPT activity. AlaAT activity was measured, using the method described above, in the leaf tissue of several of these transformants. As can be seen from Table 1, the btg-26/AlaAT/NOS plants had AlaAT activity levels that ranged from 1.63 to 3.89 times that of the wild-type, control plants. Ca2/AlaAT/NOS plants had activity levels that ranged from 1.51 to 2.95 times that of wild-type, control plants. Western blots confirmed that the transgenic plants had elevated levels of AlaAT, based on the cross reactivity of a band with the barley AlaAT antibody (not shown).

TABLE 1

Alanine aminotransferase (AlaAt) activity in primary transformants

| Plant | Activity* |
|---|---|
| btg-26/AlaAt/NOS | |
| transformant #4 | 3.89× |
| transformant #5 | 1.63× |
| transformant #7 | 1.93× |
| transformant #8 | 1.98× |
| transformant #18 | 1.63× |
| Ca2/AlaAT/NOS | |
| transformant #1 | 1.51× |
| transformant #2 | 2.77× |
| transformant #6 | 1.61× |
| transformant #7 | 2.95× |
| transformant #9 | 2.14× |
| transformant #12 | 1.91× |
| transformant #13 | 1.77× |

*Enzyme activity is expressed relative to wild-type controls

Example 3

Growth of Primary Transformants Under Normal Conditions

T1 seed from the primary transformants of the groups CaMV/AlaAT and btg-26/AlaAT were grown along with control, wild-type plants under normal conditions including planting at a 1 cm depth in 13 cm diameter plastic pots containing a soil and fertilizer mixture as described by Good and Maclagan (ibid.). These pots were placed in growth chambers under the following conditions: i) 16 h of 265 mmol $m^{-2}$ $s^{-1}$ provided by VITA-LITE U.H.O. fluorescent tubes, ii) day and night temperatures of 21° C. and 15° C. respectively, iii) relative humidity of 85%–97% and iv) daily watering with ½ strength Hoagland's solution. The only observable difference observed between the plants was the btg-26/AlaAT plants had thicker stems when compared to the controls and CaMV/AlaAT plants. No significant differences were observed between the three groups in terms of growth rate, plant or leaf size or leaf senescence at identical time points, time to maturity, seed size or seed yield.

Example 4

Growth of Primary Transformants Under Nitrogen-Starved/Drought Conditions

Figure 9:
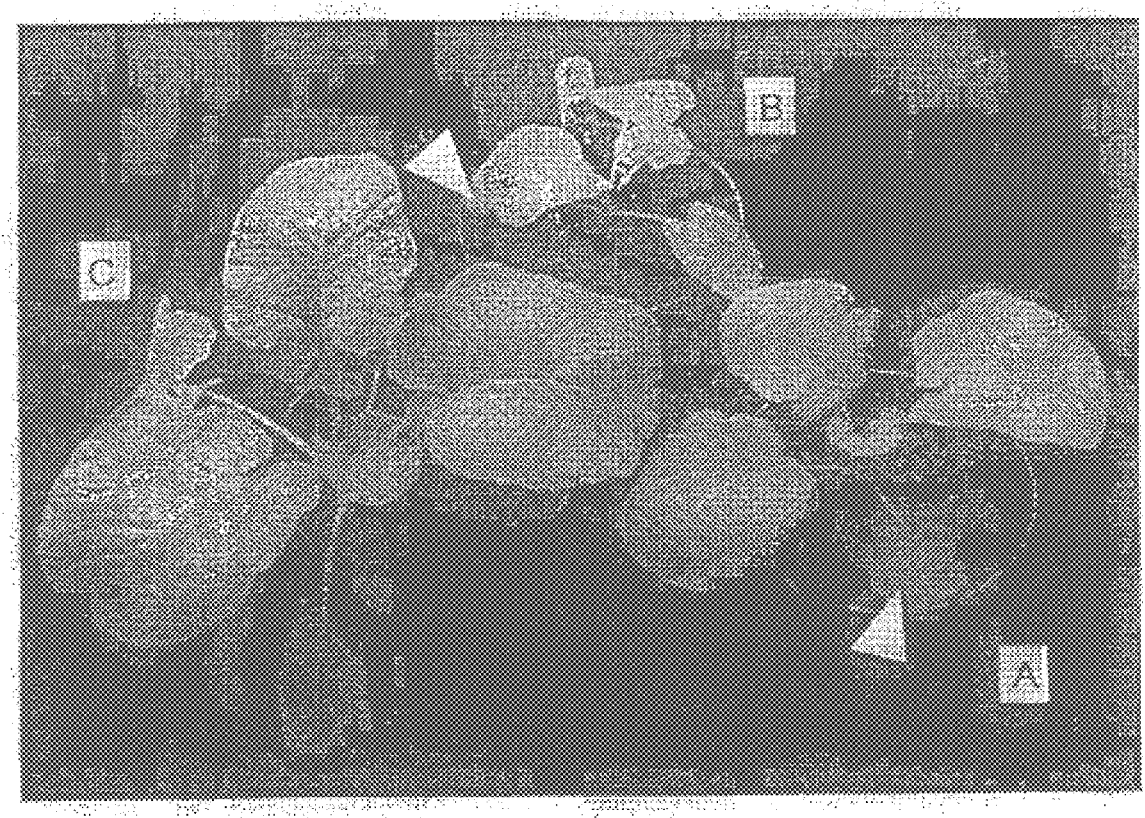
FIG. 9: *Brassica napus* plants grown under nitrogen starved conditions for three weeks followed by drought for 3 days. The plants are identified as A, B and C, as follows: Plant A is a control, wild-type plant; Plant B contains a CaMV/AlaAT construct; and Plant C contains a btg-26/AlaAT construct.

T1 seed from the primary transformants of the CaMV/AlaAT and btg-26/AlaAT groups were grown along with control, wild-type plants for four weeks under normal conditions (as noted above) and then subjected to nitrogen starvation, by watering with only water for three weeks, followed by drought for 3 days. FIG. 9 shows representative plants from the three groups after the treatment at identical time point. Plant A is a control, wild-type plant; Plant B is a CaMV/AlaAT transformed plant; and Plant C is a btg-26/AlaAT plant. It can be seen that plant C (btg-26) clearly has a faster growth rate than plants A (control) and B (CaMV/AlaAT). In addition, senescing leaves (indicated by arrows) are present on plants A and B while plant C has no senescing leaves. In summary, the following were observed in the treated btg-26/AlaAT plants when compared to the treated CaMV/AlaAT and control plants: faster growth rate; larger plants at similar time points, less senescence in the lower leaves; earlier maturity; thicker stems; larger seeds; and higher seed yields.

It will be apparent that many other changes may be made to the illustrative embodiments, while falling within the scope of the invention and it is intended that all such changes be covered by the claims appended hereto.

What is claimed is:

1. An isolated Brassica turgor gene-26 promoter element consisting of nucleotides 1–365 of SEQ ID NO:1.

2. An isolated Brassica turgor gene-26 promoter element consisting of a fragment of nucleotides 1–365 of SEQ ID NO:1 which is inducible under osmotic stress conditions.

3. A genetic construct comprising a Brassica turgor gene-26 promoter element of claims 1 or 2 operably associated with a heterologous gene.

4. A genetic construct comprising a Brassica turgor gene-26 promoter element of claims 1 or 2 operably associated with a nitrogen assimilation/metabolism enzyme coding sequence.

5. The genetic construct of claim 4, wherein the nitrogen assimilation/metabolism enzyme is selected from the group consisting of: glutamine synthetase, asparagine synthetase, glutamate 2:oxogluturate aminotransferase, asparaginase, glutamate dehydrogenase, aspartate aminotransferase and alanine aminotransferase or active modified forms thereof.

6. A method for producing a plant cell containing a promoter which is inducible under osmotic stress conditions, comprising:
transforming a plant cell with a genetic construct of claim 3 such that a plant cell containing a promoter which is inducible under osmotic stress conditions is produced.

7. A method for producing a plant regenerated from plant cells containing a promoter which is inducible under osmotic stress conditions, comprising
regenerating a plant cell containing a promoter which is inducible under osmotic stress conditions, thereby producing a plant,
wherein the plant cell was transformed with a genetic construct of claim 3.

8. A method for producing a plant cell containing a promoter which is inducible under osmotic stress conditions, comprising:
transforming a plant cell with a genetic construct of claim 4 such that a plant cell containing a promoter which is inducible under osmotic stress conditions is produced.

9. A method for producing a plant regenerated from plant cells containing a promoter which is inducible under osmotic stress conditions, comprising
regenerating a plant cell containing a promoter which is inducible under osmotic stress conditions, thereby producing a plant,
wherein the plant cell was transformed with a genetic construct of claim 4.

10. A method for producing a plant cell containing a promoter which is inducible under osmotic stress conditions, comprising:
transforming a plant cell with a genetic construct of claim 5 such that a plant cell containing a promoter which is inducible under osmotic stress conditions is produced.

11. A method for producing a plant regenerated from plant cells containing a promoter which is inducible under osmotic stress conditions, comprising
regenerating a plant cell containing a promoter which is inducible under osmotic stress conditions, thereby producing a plant,
wherein the plant cell was transformed with a genetic construct of claim 5.

* * * * *

UNITED STATES PATENT AND TRADEMARK OFFICE
CERTIFICATE OF CORRECTION

PATENT NO.     : 6,084,153
DATED          : July 4, 2000
INVENTOR(S)    : Allen G. Good et al.

It is certified that error appears in the above-identified patent and that said Letters Patent is hereby corrected as shown below:

<u>Title page,</u>
Item [22], after "Filed: Feb.", delete "14" and insert -- 13 --.

Signed and Sealed this

Twenty-sixth Day of February, 2002

Attest:

JAMES E. ROGAN
*Director of the United States Patent and Trademark Office*

*Attesting Officer*

```
                             SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 365 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

GTCGACCTGC AGGTCAACGG ATCCTAATCG GGGTATATCC CGACCCGGAA AAAGAAACGT      60

AGGACACGTG ACAAAACTTC ATATGATCCG AGTGAATCAA GCCAAAAGGG GGATTGACAC     120

AACAGCTCAG CTTTCGTTTT CGGTCCAATC GCTGTTCCAA CTTTACTTAC AAGTCGTACA     180

CGTCTCTCTC TCTCTCTCTC TCTCTCACTC ACTTCCTCTT ATAAAGACTC TCTGATCAAA     240

CGTATAATCG GAAAACTCCA TTCTTTGATA CCATCGATAA TACTAAGAGA GGTGATTGAT     300

TCTTTAATCA CTGTTTGATA TCCTTAACTT TGATCCATTT ACTCTGTTCA ATCATTTTTG     360

TAGAG                                                                 365

(2) INFORMATION FOR SEQ ID NO: 2:

(i) SEQUENCE CHARACTERISTICS:
        (A) LENGTH: 1701 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GGCCACAAAA CCGCGGAAAG AGATAGACGG ACAGCTAGAG GCGTCGGAAG ATACTCGCTG      60

CTCTGCCGCC CCCTTCGTCT TAGTTGATCT CGCCATGGCT GCCACCGTCG CCGTGGACAA     120

CCTGAACCCC AAGGTTTTAA AATGTGAGTA TGCTGTGCGT GGAGAGATTG TCATCCATGC     180

TCAGCGCTTG CAGGAACAGC TAAAGACTCA ACCAGGGTCT CTACCTTTTG ATGAGATCCT     240

CTATTGTAAC ATTGGGAACC CACAATCTCT TGGTCAGCAA CCAGTTACAT TCTTCAGGGA     300

GGTTCTTGCC CTTTGTGATC ATCCAGACCT GTTGCAAAGA GAGGAAATCA AAACATTGTT     360

CAGTGCTGAT TCTATTTCTC GAGCAAAGCA GATTCTTGCC ATGATACCTG GAAGAGCAAC     420

AGGAGCATAC AGCCATAGCC AGGGTATTAA AGGACTTCGT GATGCAATTG CTTCTGGGAT     480

CGCTTCACGA GATGGATTCC CTGCTAATGC TGATGACATT TTTCTCACAG ATGGAGCAAG     540
```

-continued

```
TCCTGGGGTG CACCTGATGA TGCAATTACT GATAAGGAAT GAGAAAGATG GCATTCTTGT      600

CCCGATTCCT CAGTACCCCT TGTACTCGGC TTCCATAGCT CTTCATGGCG GAGCTCTTGT      660

CCCATACTAT CTCAATGAAT CGACGGGCTG GGGTTTGGAA ACCTCTGATG TTAAGAAGCA      720

ACTTGAAGAT GCTCGGTCAA GAGGCATCAA CGTTAGGGCT TTGGTGGTTA TCAATCCAGG      780

AAATCCAACT GGACAGGTAC TTGCTGAAGA AAACCAATAT GACATAGTGA AGTTCTGCAA      840

AAATGAGGGT CTTGTTCTTC TAGCTGATGA GGTATACCAA GAGAACATCT ATGTTGACAA      900

CAAGAAATTC CACTCTTTCA AGAAGATAGT GAGATCCTTG GGATACGGCG AGGAGGATCT      960

CCCTCTAGTA TCATATCAAT CTGTTTCTAA GGGATATTAT GGTGAGTGTG GTAAAAGAGG     1020

TGGTTACTTT GAGATTACTG GCTTCAGTGC TCCAGTAAGA GAGCAGATCT ACAAAATAGC     1080

ATCAGTGAAC CTATGCTCCA ATATCACTGG CCAGATCCTT GCTAGTCTTG TCATGAACCC     1140

ACCAAAGGCT AGTGATGAAT CATACGCTTC ATACAAGGCA GAAAAAGATG GAATCCTCGC     1200

ATCTTTAGCT CGTCGTGCGA AGGCATTGGA GCATGCATTC AATAAACTTG AGGGAATTAC     1260

TTGCAACGAG GCTGAAGGAG CAATGTACGT GTTCCCTCAA ATCTGTCTGC CACAGAAGGC     1320

AATTGAGGCT GCTAAAGCTG CTAACAAAGC ACCTGATGCA TTCTATGCTC TTCGTCTCCT     1380

CGAGTCGACT GGAATCGTCG TTGTCCCTGG ATCAGGATTT GGCCAGGTTC CTGGCACATG     1440

GCACTTCAGG TGCACGATCC TTCCGCAGGA GGATAAGATC CCGGCAGTCA TCTCCCGCTT     1500

CACGGTGTTC CATGAGGCGT TCATGTCAGA GTATCGTGAC TAAACTGGTG CAACATGTGG     1560

GATTACATAC AACCCTCATG GGGTTTTCGT AGGCGTTCTT GGTTTTGCCC CCCCCCCCCT     1620

TCTCTCTCTC TCTCTCTCTG ACAGCATCCT CCTCTAGATG AGACAAAATA AAGCAAAGCC     1680

ATGTCATCCT TAAAAAAAAA A                                               1701
```